(12) United States Patent
Boyke

(10) Patent No.: US 9,968,529 B2
(45) Date of Patent: May 15, 2018

(54) ANTIPERSPIRANT/DEODORANT COMPOSITION

(71) Applicant: Colgate-Palmolive Company, New York, NY (US)

(72) Inventor: Christine Boyke, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days. days.

(21) Appl. No.: 15/103,720

(22) PCT Filed: Dec. 11, 2013

(86) PCT No.: PCT/US2013/074277
§ 371 (c)(1),
(2) Date: Jun. 10, 2016

(87) PCT Pub. No.: WO2015/088503
PCT Pub. Date: Jun. 18, 2015

(65) Prior Publication Data
US 2016/0303008 A1 Oct. 20, 2016

(51) Int. Cl.
*A61K 8/26* (2006.01)
*A61K 8/25* (2006.01)
*A61Q 15/00* (2006.01)
*A61K 8/49* (2006.01)
*A61K 8/97* (2017.01)

(52) U.S. Cl.
CPC .................. *A61K 8/26* (2013.01); *A61K 8/25* (2013.01); *A61K 8/4973* (2013.01); *A61K 8/97* (2013.01); *A61Q 15/00* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 4,151,272 A | 4/1979 | Geary et al. | |
| 4,425,328 A | 1/1984 | Nabial | |
| 4,777,034 A | 10/1988 | Olivier et al. | |
| 5,176,903 A * | 1/1993 | Goldberg | A61K 8/11 424/401 |
| 5,605,682 A | 2/1997 | Ross et al. | |
| 6,428,777 B1 * | 8/2002 | Boyle | A61K 8/02 424/400 |
| 2002/0155078 A1 | 10/2002 | Avendano et al. | |
| 2008/0187562 A1 * | 8/2008 | Fan | A61Q 15/00 424/401 |

FOREIGN PATENT DOCUMENTS

| | | | |
|---|---|---|---|
| DE | 102010038357 | 1/2012 | |
| DE | 102010038358 | 1/2012 | |
| EP | 0319168 | 6/1989 | |
| EP | 0570085 | 11/1993 | |
| EP | 2189149 | 5/2010 | |
| FR | 2975907 A1 * | 12/2012 | A61K 8/25 |
| WO | WO 2009/037566 | 3/2009 | |
| WO | WO 2011/040911 | 4/2011 | |
| WO | WO 2011 076569 | 6/2011 | |
| WO | WO 2013/045270 | 4/2013 | |
| WO | WO 20131045269 | 4/2013 | |

OTHER PUBLICATIONS

FR2975907A1 EPO English Translation ([retrieved from on-line website: http://translationportal.epo.org/emtp/translate/?ACTION=description-retrieval&COUNTRY=FR&ENGINE=google&FORMAT=docdb&KIND=A1&LOCALE=en_EP&NUMBER=2975907&OPS=ops.epo.org/3.1&SRCLANG=fr&TRGLANG=en, last visit Nov. 27, 2016]).*
DE 102010038357 A1 Google English Translation ([retrieved from on-line website: https://www.google.ch/patents/DE102010038357A1?cl32 en&hl=de]).*
Dadd, "Is Potassium Alum Aluminum-Free", potassium alum which is also called as potassium aluminum sulfate) is a natural mineral salt, 2013,([retrieved from on-line website: http://www.debralynndadd.com/q-a/is-potassium-alum-aluminum-free/]).*
Bentonites ([retrieved from on-line website: http://www.claysandminerals.com/materials/bentonites, last visit Mar. 22, 2017]).*
Hetorite ([retrieved from on-line website: https://www.skinstore.com/beauty-center/ingredients/hectorite.list , last visit Mar. 22, 2017], p. 13).*
International Search Report and Written Opinion for International Application No. PCT/US2013/074277 dated Aug. 8, 2014.

* cited by examiner

*Primary Examiner* — Ernst V Arnold
*Assistant Examiner* — Kyung S Chang

(57) ABSTRACT

Provided herein is a soft solid or solid antiperspirant/deodorant composition comprising alum, a clay and talc, wherein the clay is present in an amount of 0.1 weight % to 3 weight % by total weight of the composition, and wherein the talc is present in an amount of 10 wt. % to 25 weight % by total weight of the composition. The combination of clay and talc effectively suspends alum in the composition, enabling an even distribution of the alum through the composition.

30 Claims, No Drawings

ANTIPERSPIRANT/DEODORANT COMPOSITION

BACKGROUND

Antiperspirant and/or deodorant compositions are generally applied to an axillary region to limit perspiration and/or to limit or kill bacteria in this region. In this way, body odor caused by bacterial growth is limited or at least reduced.

Antiperspirants and/or deodorants can be delivered topically in solid or soft solid form using, for example, a stick applicator.

'Alum' represents a class of naturally occurring chemical compounds typically having the formula $AM(SO_4)_2 \cdot xH_2O$, where A is a monovalent cation such as potassium, sodium or ammonium, and M is a trivalent metal ion such as aluminum and x is typically 12. Alum is known to have deodorant, astringent and antiperspirant activity, and therefore, it is often used in antiperspirant/deodorant compositions.

Typically during the manufacture of a solid or soft solid antiperspirant/deodorant composition, the ingredients of the composition are combined and heated to melt the components, and the melted components are mixed. After mixing, the molten composition may be poured directly into dispensers, where it is allowed to cool and harden. The dispersers are then capped to preserve the solid compositions until use.

However, when alum is present in the solid or soft solid antiperspirant/deodorant compositions, it has a tendency to settle at the bottom of the dispenser before the compositions harden into a solid. This leads to an uneven distribution of alum through the solid or soft solid form, with an increased amount of alum at one end of the form as compared to the other end.

Clay materials such as bentonite and hectorite are often used as suspending, agents in antiperspirant/deodorant compositions. However, these materials are expensive.

Therefore, there is the need to provide improved, cost-effective antiperspirant/deodorant compositions comprising alum which resist settling of the alum.

BRIEF SUMMARY

The present inventors have found that a specific combination of talc and a clay material is effective in suspending alum in antiperspirant/deodorant compositions. In particular, when talc is used in combination with a day material a relatively small amount of the clay material is required to spend the alum, thereby reducing the cost of manufacture of the antiperspirant/deodorant compositions.

Accordingly, in a first aspect, provided is a soft solid or solid antiperspirant/deodorant composition comprising alum, a clay and talc.
wherein the clay is present in an amount of 0.1 weight % to 3 weight % by total weight of the composition, and
wherein the talc is present in amount of 10 wt. % to 25 weight % by total weight of the composition.

Typically the clay comprises one or more of: hectorite, bentonite and derivatives thereof. Preferably, the composition is a solid composition.

Preferably, the composition comprises alum in an amount of 1 weight % to 10 weight % by total weight of the composition. More preferably, the composition comprises alum in an amount of 1 weight % to 3 weight % by total weight of the composition.

Preferably, the composition comprises a clay in an amount of 0.5 weight % to 2 weight % by total weight of the composition. More preferably, the composition comprises a clay in an amount of 0.5 weight % to 1 weight % by total weight of the composition.

Preferably, the composition comprises talc in an amount of 13 weight % to 20 weight % by total weight of the composition. More preferably, the composition comprises talc in an amount of 15 weight % to 18 weight % by total weight of the composition.

Optionally, the alum is selected from potassium alum (potassium aluminum sulfate), sodium alum (sodium aluminum sulfate) and the ammonium alum (ammonium aluminum sulfate). Preferably, the alum comprises potassium alum.

Typically, the composition comprises propylene carbonate. Optionally, the weight ratio of the clay to propylene carbonate is about 3:1.

Optionally, the composition comprises at least one gellant. Further optionally, the gellant is selected from a fatty alcohol, a hydrocarbon of the formula $C_nH_{2n+2}$, and mixtures thereof, wherein n is 20-100 and the hydrocarbon is 90% linear. Still further optionally the gellant is present in an amount of 15 weight % to 30 weight % by total weight of the composition.

Optionally, the composition further comprises at least one emollient. Further optionally, the emollient is selected from a polypropylene-based glycol ether, an alkyl benzoate, cyclomethicone and mixtures thereof. Still further optionally, the alkyl benzoate is selected from a $C_{12}$ to $C_{15}$ alkyl benzoate and mixtures thereof. Preferably, the composition comprises at least one emollient in an amount of 10 wt. to 20 wt. % by total weight of the composition.

Optionally, the composition comprises at least one plant oil. Optionally, the plant oil comprises palm kernel oil. Preferably, the palm kernel oil is present in an amount of 25 weight % to 35 weight % by total weight of the composition. Further optionally, the plant oil comprises at least one hydrogenated plant oil. Typically, the hydrogenated plant oil is present in an amount of up to 10 wt. % by total weight of the composition. Preferably, the hydrogenated plant oil is selected from hydrogenated castor oil, hydrogenated soybean oil, and mixtures thereof.

In a second aspect provided is a deodorant or antiperspirant product comprising the composition of any preceding claim in a suitable package. Preferably, the product is a stick product.

In a third aspect, provided is a method of reducing odor/perspiration in a subject comprising applying a composition as defined herein to an axillary area of the subject.

In a fourth aspect, provided is a use of a composition as defined herein as a deodorant or an antiperspirant.

In a fifth aspect, provided is a use of a combination of a clay and talc in an antiperspirant/deodorant composition for suspending alum in the antiperspirant/deodorant composition,
wherein the clay is present in an amount of 0.1 weight % to 3 weight % by total weight of the composition, and
wherein the talc is present in an amount of 10 wt. % to 25 weight % by total weight of the composition.

The composition may be as defined herein.

In a sixth aspect, provided is a method of suspending alum in a deodorant/antiperspirant composition comprising incorporating into the composition a combination of a clay and talc, wherein the clay is incorporated into the composition in an amount of 0.1 weight % to 3 weight % by total weight of the composition, and wherein the tale is incorporated into the composition in an amount of 10 wt. % to 25 weight % by total weight of the composition.

DETAILED DESCRIPTION

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The solid or soft solid antiperspirant/deodorant composition comprises alum, a clay and talc, wherein the clay present in an amount of 0.1 weight % to 3 weight % by total weight of the composition, and wherein the talc is present in an amount of 10 wt. % to 25 weight % by total weight of the composition.

Alum

The term 'alum' as used herein denotes chemical compounds typically having the formula $AM(SO_4)_2 \cdot 12H_2O$, where A is a monovalent cation such as potassium, sodium or ammonium, and M is a trivalent metal ion such as aluminum. The extent of hydration may vary.

In one embodiment, the compositions may comprise potassium alum (potassium aluminum sulfate), sodium alum (sodium aluminum sulfate), ammonium alum (ammonium aluminum sulfate) or mixtures thereof. Preferably, the compositions comprise potassium alum (potassium aluminum sulfate) due to its superior astringent properties.

Typically, alum is present in an amount of 1 weight % to 10 weight % by total weight of the composition. In some embodiments, alum is present in an amount of from 2 weight % or 3 weight % to 8 weight % or from 2 weight % or 3 weight % to 6 weight % by total weight of the compostion. In other embodiments, alum is present in an amount of from 1 weight % to 5 weight %, or from 2 weight % to 5 weight %, or from 3 weight % to 5 weight %, or from 4 weight % to 5 weight % by total weight of the composition. In yet further embodiments, alum is present in an amount of from 1 weight % to 3 weight %, or from 1 weight % to 4 weight % by total weight of the composition.

As discussed below, the combination of talc and clay effectively prevents the settling of alum thus allowing it to be distributed evenly throughout the solid or soft solid form of the composition. When the amount of alum is as defined herein, there is an effective suspension of the alum through the solid or soft solid form, with effective antiperspirant/deodorant activity throughout the solid or soft solid form.

Clay and Talc

The compositions comprise a clay material and talc. The clay and talc, in combination, assist in filling the void space between alum particles, thus aiding their suspension.

The clay is preferably a hydrophobic montmorillonite clay such as bentonite or hectorite, or derivatives or mixtures thereof. Bentonite and hectorite clays are commercially available. Examples of days that may be used include Bentone® 27 V CG.

Clay is typically present in the compositions in an amount of 0.1 weight % to 3 weight %, or from 0.5 weight % to 3 weight %, or from 1 weight % to 3 weight %, or from 1 weight % to 2 weight % by total weight of the composition.

In some embodiments, the clay is present in an amount of 0.5 weight % to 2 weight %, or from 0.5 weight % to 1 weight % by total weight of the composition. In other embodiments, the clay is present in an amount of 0.1 weight %, 0.2 weight %, 0.3 weight %, 0.4 weight %, or 0.5 weight % to 1 weight % by total weight of the compostion. In further embodiments, the clay is present in an amount of 0.1 weight %, 0.2 weight %, 0.3 weight %, 0.4 weight %, or 0.5 weight % to 2 weight % by total weight of the composition.

Talc is typically present in the compositions in an amount of 10 weight % to 25 weight % or from 10 weight % to 20 weight % or from 15 weight % to 20 weight % by total weight of the composition. In some embodiments, talc is present in the compositions in an amount of 13 weight % to 20 weight %, or from 15 weight % to 18 weight % by total weight of the composition.

The present inventors have found that when using the combination of clay and talc as defined herein, alum is effectively suspended in antiperspirant/deodorant compositions in their molten state such that on cooling to a solid or soft solid form, the alum becomes evenly distributed throughout the form. The present inventors have found that when using the specific combination of clay and talc, only a relatively small amount of clay is required to suspend alum effectively in the molten composition. Thus, the manufacturing costs of the compositions are reduced. Furthermore, when the concentration of clay is increased above the amounts defined herein, the composition becomes too thick to effectively mix the ingredients and form a homogenous suspension. The resulting solid or soft solid form is also undesirably hard when using clay in high amounts. Thus, the use of a relatively low amount of clay in combination with talc, as defined herein, advantageously allows a homogenous dispersion of ingredients in the solid or soft solid form, and provides a solid or soft solid form with a desirable hardness.

In a particular embodiment, propylene carbonate is further incorporated into the compositions. Propylene carbonate activates the clay and enhances the suspension capacity of the clay. Typically, the weight ratio of clay to propylene carbonate in the compositions ranges from 4:1 to 2:1 and is preferably 3:1. Thus, in some embodiments, the compositions comprise propylene carbonate in an amount of 0.03 weight % to 1 weight % or from 0.1 weight % to 0.5 weight % or from 0.2 weight % to 0.5 weight % or from 0.3 weight % to 0.5 weight % by total weight of the composition.

Gellants

Gellants can optionally be included in the composition. Gellants are those materials known in the art that structure the composition. Examples include, but are not limited to, waxes, a hydrocarbon wax, esters of fatty acids, triglycerides, or other cosmetically acceptable materials, which are solid or semi-solid at room temperature and provide a consistency suitable for application to the skin. Plant oils may behave as gellants, and these are discussed separately below.

The hydrocarbon wax can be a hydrocarbon of the formula $C_nH_{2n+2}$, wherein is 20-100 and the hydrocarbon is at least 90% linear. In one embodiment, the hydrocarbon is a paraffin. In another embodiment, the hydrocarbon is polyethylene. An example of a polyethylene can be found in U.S. Pat. No. 6,503,491. In another embodiment, the polyethylene has an average molecular weight of about 300 to about 3000 Da and a melting point of about 50 to about 129° C. In one embodiment, the hydrocarbon is synthetically made from methylene to form a polymethylene. Preferably, the gellant is polyethylene or polymethylene.

The fatty alcohol can be any fatty alcohol. In one embodiment, the fatty alcohol is stearyl alcohol or docosyl alcohol (behenyl alcohol).

In another embodiment, the gellant includes hydrogenated castor oil (castor wax). In certain embodiments, the melting point of the castor wax is 70° C. to 90° C., or 70° C. to 80° C.

The gellants may be incorporated into the compositions in a total amount of 15 weight % to 30 weight % or from 20 weight % to 30 weight % by total weight of the composition.

Fatty Acids

In one embodiment, the compositions comprise one or more fatty acids. The fatty acid can be selected from any $C_{16}$ to $C_{18}$ saturated fatty acid. In some embodiments, the saturated fatty acid is stearic acid and/or palmitic acid. In one embodiment the saturated fatty acid is palmitic acid. The amount of fatty acid in the composition may be in an amount of up to 7 wt. % of the composition. In other embodiments, the amount of fatty acid may be at least 1, 2, 3, 4, 5, or 6 weight % up to 7 weight % of the composition.

Plant Oils

The compositions may include plant oil. By plant oil it is meant that the oil is obtained from a plant. Alternatively, the plant oil can be made by blending oil components to obtain an oil that is substantially similar in composition to a plant oil. By substantially similar, it is meant that the manufactured oil contains at least 50 wt. % (or at least 60, 70, 80, 90, 95, 98, or 99 wt. %) of the components that are found in the plant oil that it is designed to mimic.

In certain embodiments the plant oil has a melting point below 40° C. or below 35° C. or below 30° C.

Examples of the plant oil include, but are not limited to, palm kernel, coconut, avocado, canola, corn, cottonseed, olive, palm, hi-oleic sunflower, mid-oleic sunflower, sunflower, palm stearin, palm kernel olein, safflower, and babassu oils. In one embodiment, palm kernel oil is the selected oil. In another embodiment, coconut oil is the selected oil. In another embodiment, the plant oil is a combination of palm kernel oil and coconut oil.

In certain embodiments, the plant oil is selected to be one that contains at least 40 wt. % $C_{12}$-$C_{14}$ fatty acids. These oils will provide stick products with greater strength on a weight basis. In other embodiments the oil is selected to have high levels of saturation. High levels of unsaturation could result in undesired fragrance when the unsaturated bonds become saturated over time. In certain embodiments, the amount of unsaturated components in the oil is no more than 20, 19, 18, 17, 16, 15, 14, 13, 12, 11, or 10 wt. % of the oil. Suitable plant oils are described in further detail in WO2011/040909.

The amount of plant oil in the composition may be in an amount of at least 10 wt. % up to 40 wt. of the composition. In certain embodiments, the amount of plant oil is 15 weight % to 40 weight % or 20 weight % to 40 weight % or 25 weight % to 45 weight % or 30 weight % to 45 weight %. Optionally the amount of palm kernel oil in the compositions is from 25% to 35% by weight of the composition. In certain embodiments, the amount of plant oil is greater than the amount of volatile silicone in the compositon, which is discussed below.

Other plant oils iuchde hydrogenated plant oils. In one embodiment, the hydrogenated oil is hydrogenated soybean oil. In other embodiments, the compositions comprise a hydrogenated plant oil selected from hydrogenated castor oil, hydrogenated soybean oil, and mixtures thereof. In one embodiment, the hydrogenated soybean oil is almost, but not fully hydrogenated. The amount of hydrogenation is measured by the iodine value. The iodine value can be measured by the standard test method ASTM D5554-95 (2006). In one embodiment, the iodine value of the hydrogenated soybean oil used herein is greater than 0 to 20. In one embodiment, the iodine value is 1 to 5. In another embodiment, the soybean oil is fully hydrogenated with an iodine value of 0. In another embodiment, the iodine value is up to 20. Reference is made to United States Patent Publication No. 2008/0187504A1.

In one embodiment, the plant oil includes a partially hydrogenated soybean oil having an iodine value in the range of about 75 to about 80. This partially hydrogenated soybean oil can be obtained from Cargill under the product designation S-500. Reference is made to United States Patent Publication No. 2008/0187503A1. This material has a typical fatty acid distribution shown in the table below. Amounts shown are in % by weight.

| | |
|---|---|
| C16:0 | 10.5-11.2 |
| C18:0 | 6.8-7.5 |
| C18:1 | 61-65 |
| C18:2 | 16-19 |
| C18:3 | 0-0.2 |
| Saturates | 17.5-19.5 |
| Trans | 34-39 |

The compositions may comprise a hydrogenated plant oil in an amount of up to 10 weight % or up to 5 weight %.

In one embodiment, suitable gelation is achieved by using a combination of a hydrogenated soybean oil with a hydrocarbon as defined above. Reference is made to United States Patent Publication No. 2008/0187504A1.

Emollients

The compositions may contain one or more emollients in any desired amount to achieve a desired emollient effect. For example, the compositions may include at least one emollient in an amount of 10 weight % to 15 weight % or 10 weight % to 20 weight % by total weight of the composition. Emollients are known in the art and are used to impart a soothing effect on the skin. Non-volatile emollients are preferable. Classes of non-volatile emollients include non-silicone and silicone emollients. Non-volatile, non-silicone emollients include alkyl benzoate emollients such as $C_{12-15}$ alkyl benzoate. The non-volatile silicone material can be a polyethersiloxane, polyalkyarylsiloxane or polyethersiloxane copolymer. An illustrative non-volatile silicone material is phenyl trimethicone. Non-limiting examples of emollients can be found in U.S. Pat. No. 6,007,799. Examples include, but are not limited to, PPG-14 butyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl) adipate), Di-(2-ethyl hexyl) succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, and hydroxyethyl stearate amide.

Volatile Silicone

Compositions can include a volatile silicone emollient. In one embodiment, the volatile silicone is a volatile cyclic polydimethylsiloxane, e.g., cyclopentasiloxane. By volatile material it is meant that the material has a measurable vapor pressure at ambient temperature. Preferably, the volatile cyclic polydimethylsiloxane is cyclomethicone. Various types of cyclomethicones may be used. Illustratively and not by way of limitation, the volatile silicones are one or more members selected from cyclic polydimethylsiloxanes such as those represented by Formula I:

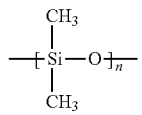

where n is an integer with a value of 3-7, particularly 5-6. Illustrative examples of suitable cyclomethicones are DC-345 and DC-245, manufactured by Dow Coming Corporation, Midland, Mich. These types include a tetramer (oetylmethylcyclotetrasiloxane) and a pentamer (decamethylcyclopentasiloxane). In one embodiment, the amount of volatile silicone in the composition is greater than 0 up to 40 wt. % by total weight of the composition. In another embodiment, the amount is less than 40, 35, 30, 25, 20, 15, 10, 5, or 1 wt. % of the composition. In another embodiment, the combined amount of the plant oil and volatile silicone is up to 50, 45, 40, 35, 30, 25, or 20 wt. % by total weight of the composition.

In a preferred embodiment, the compositions can contain an emollient selected from a polypropylene-based glycol ether (e.g. polypropylene butyl ether), an alkyl benzoate, preferably a $C_{12}$ to $C_{15}$ alkyl benzoate, and cyclomethicone.

Other Ingredients

The compositions may additionally include ionizable inorganic salts. These ionizable salts are of the form $M_aX_b$ where a=1 or 2 and b=1 or 2; M is a member chosen from $Na^{+1}$, $Li^{+1}$, $K^{+1}$, $Mg^{+2}$, $Ca^{+2}$, $Sr^{+2}$ and $Zn^{+2}$, and X is a member chosen from chloride, bromide, iodide, citrate, gluconate, lactate, glycinate, glutamate, ascorbate, asparate, nitrate, phosphate, hydrogenphophate, dihydrogensulfate. In certain embodiments, the salts are selected from bicarbonate, sulfate, and hydrogensulfate. In certain embodiments, the salts are selected from NaCl and $ZnCl_2$. As will be appreciated by those skilled in the art, while it may be possible under certain circumstances to add a salt directly to a portion of the mixture during manufacturing, it is desired to add the salt as a mixture or solution of the salt in a carrier or solvent, particularly water (salt pre-mix). Various concentrations of the salt pre-mix can be made.

The composition may also contain particulates which include but are not limited to, mica, fragrance encapsulates, or hydrophobically modified starches, such as aluminum starch octenyl succinate (MACKADERM™ ASTRO-DRY™ from McIntyre Group Ltd.). Usually, the average particle size does not exceed 150 micron.

Whilst alum is typically the only antiperspirant/deodorant active present in the compositions, in some embodiments, the compositions may comprise further deodorant/antiperspirant actives. Antiperspirant/deodorant actives would be known to the skilled person. For example, antiperspirant may include aluminum salts and aluminum-zirconium salts such as aluminum chlorohydrate and aluminum zirconium tetrachlorohydrex glycine. Deodorant actives may include alpha, beta unsaturated esters. Further examples of antiperspirant/deodorant actives are described in WO2011/040911.

The compositions may optionally further comprise absorbent materials such as corn starch, sodium polyacrylate and/or cotton fiber. Other materials such as fragrances, bacteriostats, bacteriosides and colorants may further be included. Known bacteriostats include baceteriostatic quaternary ammonium compounds such as 2-amino-2-methyl-1-propanol (AMP), cetyl-trimethylammomium bromide, cetyl pyridinium chloride, 2,4,4 N-trichloro-2N-hydroxydiphenylether (Triclosan) and various zinc salts.

Antioxidants may additionally be included in the compositions preferably for the maintenance of long-term stability of the compositions. Suitable antioxidants include Tinogard®, manufactured by Ciba Specialty Chemicals, Basel, Switzerland.

Methods of Manufacture and Use

The compositions may be manufactured using methods known in the art. Typically the ingredients are combined and heated to melt the components, prior to mixing to form a molten composition. Desirably, volatile materials, such as the fragrance materials, are incorporated in the composition in the latter stages of the mixing cycle, in order to avoid volatilization thereof. After mixing, the molten composition can be poured directly into dispensers, after which the composition is allowed to cool such that it hardens into a solid or soft solid form. The dispenser may then be capped to preserve the product until use.

As mentioned above, the present inventors have found that when using the combination of clay and talc as defined herein, alum becomes effectively suspended in the molten compositions without settling, such that on cooling to a solid or soft solid form, the alum becomes evenly distributed throughout the form.

Accordingly, in one arrangement, provided is a use of a combination of a clay and a talc in a deodorant/antiperspirant composition for suspending alum in the composition, in particular, when the composition is in molten or liquid form. In one embodiment, the composition may be cooled or solidified to form a solid or soft solid, and the suspension of alum in the composition is maintained in the solid or soft solid form. The amounts of clay, talc and alum, and the compositional features may be as defined herein. Further provided is a method of suspending alum in a deodorant/antiperspirant composition, particularly, a molten or liquid composition, comprising incorporating into the composition a combination of a clay and talc. In one embodiment, the method further comprises cooling or solidifying the composition to form a solid or soft solid. The suspension of alum in the composition is preferably maintained in the solid or soft solid form. The amounts of clay, talc and alum, and the compositional features may be as defined herein. By "suspending" it is meant that there is a reduced settling of alum in the composition, as compared to the settling that is in the absence of the clay and talc, such that the variation in the alum content on a weight basis in the composition is less than 30%, 20%, 15%, 10%, 9%, 8%, 7%, 6%, 5%, 4%, 3%, 2% or 1%. In one embodiment, the solid or soft solid compositions defined herein exhibit a variation in alum content on a weight basis as defined above.

In one embodiment, the composition is a solid stick or soft solid when at ambient room temperature of about 25° C., The stick form is an example of a solid form. The stick form can be distinguished from a soft solid in that, in a stick, the formulated product can retain its shape for extended time periods outside the package, the product not losing its shape significantly (allowing for some shrinkage due to solvent evaporation). The amounts of gelling or thickening agents may be adjusted in order to form a soft solid or stick.

Soft solids can be suitably packaged in containers that have the appearance of a stick, but which dispense through apertures (for example, slots or pores) on the top surface of the package. The soft solid products have also been called soft sticks or "smooth-ons", and herein, are generically called "soft solids". Reference is made to U.S. Pat. Nos. 5,102,656, 5,069,897, and 4,937,069.

In one embodiment, the composition is an anhydrous stick. By anhydrous it is meant that no separate water is added but there may be moisture associated with materials that are added to the composition. In certain embodiments, the amount of water is zero or less than 3, 2, 1, 0.5, or 0.1 wt. % by total weight of the composition.

Accordingly, in a further arrangement, provided is an antiperspirant or deodorant product comprising a composition as defined herein in a suitable package. In a preferred embodiment, the product is a stick product.

The compositions may be used as an antiperspirant or a deodorant. Accordingly, in yet another arrangement, provided is a method of reducing odor/perspiration in a subject comprising applying a composition as defined herein to an axillary area of the subject.

Compression and Strength

In one embodiment, the compression force of the composition is at least 3000 g. In other embodiments, the compression force is at least 4000 g, at least 4500 g, at least about 5000 g, at least 6000 g at least 7000 g, or at least 8000 g. Preferably, the compression force is from 3000 g to 8000 g. More preferably, the compression force is from 5000 g to 6000 g.

The compression strength of a stick product may be measured using a Texture Analyzer Model # TA-ZT21 from Texture Technologies. The compression probe is a 19 mm square end probe. A 42.5 g (1.5 oz) antiperspirant stick is selected. The antiperspirant stick is removed from the barrel and placed in a hardness sample holder. The stick is positioned such that 2.54 cm (1 inch) of the sample is exposed for the test. The cover on the hardness holder is closed and the holder positioned so that the blade comes in contact with the midpoint of the exposed sample. The measurements to be recorded are peak force and distance required to break the stick. A high force reading is indicative of increased strength. A long break distance to break is indicative of elasticity.

The 'payout' of a composition reflects the ease of transfer of the antiperspirant/deodorant material on to the underarm. In one embodiment, a stick product can provide a payout of 0.7 to 0.9 g according to a payout test on a "Payout, Glide, and Flake-off Test Machine". As used in this specification, the "Payout, Glide, and Flake-off Test Machine" refers to the system described in WO2009/045557.

The 'glide' of a composition reflects the ease of application (e.g., the amount of pressure the user has to use to deposit a required amount of deodorant material to the underarm). In one embodiment, a stick product can provide a glide of 0.8 to 1.4 g according to the glide test on the "Payout, Glide, and Flake-off Test Machine".

The "flake-off" of a composition is a measure of the weight loss of material from a sample that has been stretched. It reflects how well a material such as an antiperspirant/deodorant composition will remain on a substrate. In one embodiment, the stick product can provide a flake-off of less than 25%, 20%, 15%, 10%, or 5%. In other embodiments, the amount of flake-off is 1 to 6%.

The invention is further described in the following examples. The examples are merely illustrative and do not in any way limit the scope of the invention as described and claimed.

EXAMPLES

Example 1

Prototype Formulation is Illustrated in Table 1

TABLE 1

| Ingredient | Amount (wt. %) |
| --- | --- |
| $C_{12\text{-}15}$ Alkyl Benzoate | 5.9 |
| PPG-14 Butyl Ether | 5.9 |
| H-Soybean Oil | 2 |
| Castor Wax MP80 | 6.5 |
| PEG-8 Distearate | 3.3 |
| Stearyl Alcohol | 17 |
| Behenyl Alcohol | 0.17 |
| Cyclomethicone | 13.6 |
| Palm kernel oil | 23.3 |
| Bentone 27 VCG | 1 |
| Propylene Carbonate | 0.33 |
| Talc | 17.7 |
| Alum | 2 |
| Minors (fragrance, stabilizers, etc.) | Q.S. |

Example 2

Alum Suspension in Antiperspirant/deodorant Formulations (I)

When manufacturing antiperspirant/deodorant formulations comprising alum, it was observed that in the molten composition, there was a tendency for alum to settle. As a result, once the composition had cooled and hardened into a solid form, there was an uneven distribution of alum through the solid.

To address this problem, various thickeners and structure enhancers (test materials) were tested to determine whether the suspension of alum could be improved in the presence of these materials. The material was incorporated into a potassium aluminum sulfate (potassium alum)-containing antiperspirant/deodorant base formulation. The components of the formulation, including the test material, were heated to form a molten composition and mixed. After mixing, the molten composition was poured into an inverted dispenser (such that the dispenser cap was at the bottom), and allowed to cool such that a solid stick formed. After solidification, samples were taken from the top ⅓ of the stick (cap end) and analyzed for aluminum content. A high aluminum content at the top of the stick was indicative of alum settling.

Table 2 illustrates the effects of stearyl alcohol on the settling of alum. Approximately 10.4% of the weight of potassium aluminum sulfate (potassium alum) is aluminum. Therefore, as can be seen in Table 2, a formulation comprising 7.5 weight % potassium alum was expected to have an aluminum content of 0.78 weight % ("Al target"), assuming there was no settling of the variation, an acceptable range of aluminum content was 0.67 weight % to 0.9 weight % (15% above and below the % Al target). In the absence of stearyl alcohol, the aluminum content at the top of the stock was 1.03 weight %, which was significantly higher than the target amount and the acceptable range, indicating settling of the alum. In the presence of stearyl alcohol, there was even more settling of alum, such that the ahnninum content at the top of the stick was 1.13 weight %.

TABLE 2 effects of stearic acid on settling of alum in a base formulation

| | Base with 7.5% potassium alum | Base with 7.5% potassium alum and stearyl alcohol |
|---|---|---|
| Al target (wt. %) | 0.78 | 0.78 |
| Al range (weight %) | 0.67-0.9 | 0.67-0.9 |
| Al at top of stick (weight %) | 1.03 | 1.13 |

Other structurant materials that were tested included palmitic acid, petrolatum and hydroxymethyl cellulose.

Palmitic acid was not effective in suspending alum. In a base formulation with 5% alum (such that the aluminum target was 0.52 weight %) and palmitic acid, the aluminum content at the top of the stick was 1.14 weight %, and no aluminum was detected at the bottom of the stick. Comparable results were obtained with petrolatum.

Hydroxymethylcellulose was also ineffective in suspending alum. Formulations comprising 18 weight % hydroxymethylcellulose were too vicious to pour in their molten state, and resulted in solid forms that were "crumbly".

Example 3

Alum Suspension in Antiperspirant/deodorant Formulations (II): Talc and Clay

The procedure described in Example 2 was repeated using a base formulation, comprising 3 weight % potassium alum, 16.7 weight % talc and 1 weight % Bentone® clay (hectorite). The results are illustrated in Table 3.

TABLE 3 effects of talc and clay on settling of alum in a base formulation

| | Base with 3 weight % potassium alum 16.7 weight % talc and 1 weight % Bentone ® clay |
|---|---|
| Al target (wt. %) | 0.31 |
| Al range (weight %) | 0.26-0.36 |
| Al at top of stick (weight %) | 0.27 |

It can be seen from Table 3 that in the presence of about 17 weight % talc and 1 weight % clay, alum was effectively suspended such that the amount of aluminum at the top of the stick fell within the target/expected range.

When a comparable amount of talc was used in the absence of clay, there a visible separation of the molten formulation before pouring into the dispenser suggesting settling of the alum and/or talc.

When bentone was used in high amounts in the absence of talc (e.g. ~14 weight %), the formulation was too thick to mix the ingredients in a homogenous fashion and to pour into the dispenser.

Thus, it can be concluded that the specific combination of talc and clay (for example, in an amount of 10 wt. % to 25 weight % and 0.1 weight % to 3 weight % respectively) forms an effective system for suspending alum in antiperspirant/deodorant formulations, allowing the alum to be homogenously distributed through the formulations.

The invention claimed is:

1. An antiperspirant/deodorant composition, comprising an antiperspirant active, a clay, and talc,
    wherein the clay is selected from bentonite, hectorite, and combinations thereof, and the clay is present in an amount of 0.1 weight % to 3 weight % by total weight of the composition,
    wherein the antiperspirant active consists of compounds having the formula $AM(SO_4)_2 \cdot 12H_2O$, wherein A is a monovalent cation and M is a trivalent metal ion, and the antiperspirant active is present in an amount of 1 weight % to 10 weight % by total weight of the composition,
    wherein the talc is present in an amount of 15 weight % to 18 weight % by total weight of the composition,
    wherein the antiperspirant/deodorant composition is a solid stick or a soft stick made from cooling a molten composition, and
    wherein variation of the antiperspirant active content on a weight basis throughout the solid stick or soft stick is less than 15%.

2. The composition of claim 1, wherein the clay consists of bentonite.

3. The composition of claim 1, wherein the antiperspirant active is present in an amount of 1 weight % to 3 weight % by total weight of the composition.

4. The composition of claim 1, wherein the clay is present in an amount of 0.5 weight % to 2 weight % by total weight of the composition.

5. The composition of claim 4, wherein the clay is present in an amount of 0.5 weight % to 1 weight % by total weight of the composition.

6. The composition of claim 1, wherein the antiperspirant active consists of potassium aluminum sulfate, sodium aluminum sulfate, and ammonium aluminum sulfate.

7. The composition of claim 6, wherein the antiperspirant active consists of potassium aluminum sulfate and sodium aluminum sulfate.

8. The composition of claim 1, further comprising propylene carbonate.

9. The composition of claim 8, wherein the weight ratio of the clay to propylene carbonate is about 3:1.

10. The composition of claim 1, further comprising at least one gellant.

11. The composition of claim 10, wherein the gellant is selected from a fatty alcohol, and a hydrocarbon of the formula $C_nH_{2n+2}$, and mixtures thereof, wherein n is 20-100 and the hydrocarbon is 90% linear.

12. The composition of claim 10, wherein the gellant is present in an amount of 15 weight % to 30 weight % by total weight of the composition.

13. The composition of claim 1, further comprising at least one emollient.

14. The composition of claim 13, wherein the emollient is selected from a polypropylene-based glycol ether, an alkyl benzoate, cyclomethicone and mixtures thereof.

15. The composition of claim 14, wherein the alkyl benzoates are selected from a $C_{12}$ to $C_{15}$ alkyl benzoate and mixtures thereof.

16. The composition of claim 13, where the at least one emollient is present in an amount of 10 weight % to 20 weight % by total weight of the composition.

17. The composition of claim 1, further comprising at least one plant oil.

18. The composition of claim 17, wherein the plant oil comprises palm kernel oil.

19. The composition of claim 17, wherein the plant oil is present in an amount of 15 weight % to 40 weight % by total weight of the composition.

20. The composition of claim 17, wherein the plant oil comprises at least one hydrogenated plant oil.

21. The composition of claim 20, wherein the hydrogenated plant oil is present in an amount of up to 10 weight % by total weight of the composition.

22. The composition of claim 20, wherein the hydrogenated plant oil is selected from hydrogenated castor oil, hydrogenated soybean oil, and mixtures thereof.

23. The composition of claim 1, wherein the compression force of the composition is from 3000g to 8000g.

24. The composition of claim 23, wherein the compression force is from 5000g to 6000g.

25. A method of reducing perspiration/odor in a subject comprising applying the composition of claim 1 to an axillary area of the subject.

26. A method of producing a deodorant/antiperspirant composition comprising an antiperspirant active, a clay, and talc, including:
   heating the components to form a molten composition, and
   cooling the molten composition into a solid stick or a soft stick,
   wherein the clay is selected from bentonite, hectorite, and combinations thereof, and is incorporated into the composition in an amount of 0.1 weight % to 3 weight % by total weight of the composition,
   wherein the antiperspirant active consists of compounds having the formula $AM(SO_4)_2 \cdot 12H_2O$, wherein A is a monovalent cation and M is a trivalent metal ion, and the antiperspirant active is present in an amount of 1 weight % to 10 weight % by total weight of the composition,
   wherein the talc is incorporated into the composition in an amount of 15 weight % to 18 weight % by total weight of the composition, and
   wherein variation of the antiperspirant active content on a weight basis throughout the solid stick or soft stick is less than 15%.

27. An antiperspirant/deodorant composition, comprising an antiperspirant active, a clay, talc, at least one gellant, and at least one emollient,
   wherein the clay consists of bentonite and hectorite, and the clay is present in an amount of 0.1 weight % to 3 weight % by total weight of the composition,
   wherein the antiperspirant active consists of potassium aluminum sulfate, sodium aluminum sulfate, and ammonium aluminum sulfate, and the antiperspirant active is present in an amount of 1 weight % to 3 weight % by total weight of the composition,
   wherein the talc is present in an amount of 15 weight % to 18 weight % by total weight of the composition,
   wherein the gellant is selected from a fatty alcohol, a hydrocarbon of the formula $C_nH_{2n+2}$, and mixtures thereof, wherein n is 20-100 and the hydrocarbon is 90% linear, and wherein the gellant is present in an amount of 15 weight % to 30 weight % by total weight of the composition,
   wherein the antiperspirant/deodorant composition is a solid stick or a soft stick made from cooling a molten composition, and
   wherein variation of the antiperspirant active content on a weight basis throughout the solid stick or soft stick is less than 15%.

28. The composition of claim 27, further comprising propylene carbonate, wherein the weight ratio of the clay to propylene carbonate is about 3:1.

29. The composition of claim 28, wherein the clay is present in an amount of 0.5 weight % to 1 weight % by total weight of the composition.

30. The composition of claim 29, further comprising at least one hydrogenated plant oil, wherein the hydrogenated plant oil is present in an amount of 2 weight % to 10 weight % by total weight of the composition, and wherein the hydrogenated plant oil consists of hydrogenated castor oil and hydrogenated soybean oil.

* * * * *